United States Patent [19]
Hiltebrandt et al.

[11] Patent Number: 5,113,846
[45] Date of Patent: May 19, 1992

[54] ORGAN MANIPULATOR

[75] Inventors: Siegfried Hiltebrandt, Knittlingen; Johann Wolf, Bretten, both of Fed. Rep. of Germany

[73] Assignee: Richard Wolf GmbH, Knittlingen, Fed. Rep. of Germany

[21] Appl. No.: 724,834

[22] Filed: Jul. 2, 1991

[51] Int. Cl.⁵ .................................. A61B 17/02
[52] U.S. Cl. .......................... 128/20; 604/105
[58] Field of Search .......... 606/110, 113, 198; 604/105; 128/20

[56] References Cited

U.S. PATENT DOCUMENTS

| | | | |
|---|---|---|---|
| 650,496 | 5/1900 | Stohlmann et al. | 606/110 |
| 929,833 | 8/1909 | Combs | 606/110 |
| 1,324,976 | 12/1919 | Oesterwirtz | 606/110 |
| 1,919,120 | 7/1933 | O'Connor et al. | 128/20 |
| 2,053,863 | 9/1936 | Grosso | 128/20 |
| 2,072,346 | 3/1937 | Smith | 604/105 |
| 3,903,892 | 9/1975 | Komiya | 606/110 |
| 4,043,338 | 8/1977 | Homm et al. | 604/105 |
| 4,648,402 | 3/1987 | Santos | 606/198 |
| 4,660,571 | 4/1987 | Hess et al. | 604/105 |
| 5,002,560 | 3/1991 | Machold et al. | 606/198 |

Primary Examiner—Paul J. Hirsch
Attorney, Agent, or Firm—Cohen, Pontani, Lieberman & Pavane

[57] ABSTRACT

An organ manipulator is described for exposing an organ situated in a body cavity to be investigated or treated. The manipulator has a retractor body comprising a multi-joint lever system of articulated arms connected to one another, to be pivotally movable and which can be transformed from a axial position for introduction into the body cavity into an open position, in which is possible for the articulated arms to assume a flat triangular shape.

5 Claims, 1 Drawing Sheet

ORGAN MANIPULATOR

BACKGROUND OF THE INVENTION (a) Field of the Invention

The present invention relates to a medical instrument for manipulating internal organs of the body, having a retractor body arranged at the distal end of a rod, guided in a shaft which is provided with a handle at its proximal end and is guided to be axially displaceable in the shaft, to bring the retractor body into either a straight or an open position.

(b) Description of the Prior Art

Endoscopic operations in the abdominal cavity on the one hand assume that a body cavity is dilated by means of body cavity gas, and on the other hand that there is free access to the organ to be investigated or treated. If free access to a certain organ is not possible, that is, if the part or region of the organ or the entire organ to be investigated and to be treated is hidden by another organ, the obscured region of the organ concerned must be exposed.

The organ to be treated is exposed or manipulated according to the known art using forceps or, as described in German Patentschrift 3 709 706, by means of three spring resilient elements designed like fingers which have spherical elements at their distal ends, that is directly at the ends engaging the organ or the like to be manipulated, to avoid injury to the organ.

The previously known disadvantage of the manipulators is that they allow only inadequate manipulation because of the insufficient transfer of force and may also cause injury at least in some cases. The danger that the individual fingers will bend as a result of the engaging force exists in particular in the manipulator of German Patentschrift 3 709 706, due to the relatively low mechanical stability. The finger elements, which can be included in the outer shaft are subject to uncontrolled movement due to bending when being removed from the shaft, as a result of which the usability is considerably impaired. A further disadvantage of this manipulator resides in the fact that the retracting force of the retractor elements is derived from the spring bias of the same, and the retracting force is therefore fixed in each case at its maximum and cannot be influenced. This may result in insufficient retracting force, so that if the surgeon is unaware that the retractor is at an equilibrium of the retracting force and the retracting resistance, with the result that the retractor path will not be limited by the shaft of the instrument, but rather by the retracting resistance, so that the retracting force then strains the manipulated organ in an uncontrolled manner. This may lead to organ damage.

It is therefore an object of the present invention to address these disadvantages associated with known retractors, and enable, on the one hand relatively high forces to be exerted when the organ is manipulated, and on the other hand to avoid possible improper handling at the manipulator from leading to injury of the organ or the like.

SUMMARY OF THE INVENTION

This object is achieved in accordance with the invention by a medical instrument for manipulating internal organs of the body having a retractor body arranged at the distal end of a rod, guided in a shaft, which is provided with a handle at its proximal end and is guided to be axially displaceable in the shaft, to bring the retractor body into a straight or open position, characterised in that the retractor body has a multi-joint lever system of articulated arms connected to one another to be pivotally movable, which articulated arms can be brought from a straight position into a retracted position.

Preferably, the multi-joint lever system comprises four articulated arms, in each case two of these being connected to one another by means of a central joint and being located on opposing sides of the rod guided in the shaft and in each case one end of the two articulated arm pairs is pivotally connected to the distal end of the rod, and the other end is pivotally connected to the distal end of the shaft.

The articulated connections have hinge pins, with the hinge pin arranged in the region of the distal end of the shaft, engaging the rod in the region of a longitudinal slot situated in it and being fixed in the shaft.

Conveniently, the hinge pins in the region of the distal end of the rod or of the shaft are arranged in the plane of the central axis of the rod and the hinge pins forming the central joints in the axially aligned position of the articulated arms are arranged outside of the plane of the central axis of the rod.

The articulated arms pivotally connected to the distal end of the rod may act as exposing rods for the articulated arms, the articulated arms being essentially aligned with one another in the maximum retracting position.

It is possible with the aid of an instrument of this type to push aside an organ to be manipulated with defined force effect, the retractor path of the retractor body being clearly controllable as a result of the direct and inevitable reversal of longitudinal movement of the rod in the retractor movement and the retractor position being statically fixable.

BRIEF DESCRIPTION OF THE DRAWINGS

A preferred embodiment of this invention will now be described, by way of example only, with reference to the drawings in which.

DESCRIPTION OF THE PREFERRED EMBODIMENT

Figure 1:
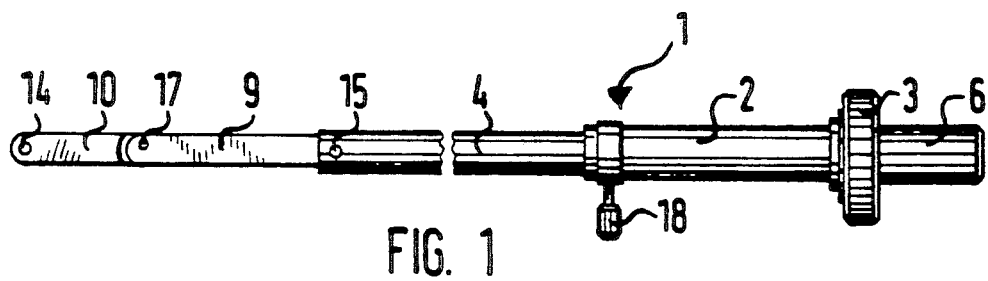
FIG. 1 shows a side view of the manipulator with a straight retractor body.
Figure 2:
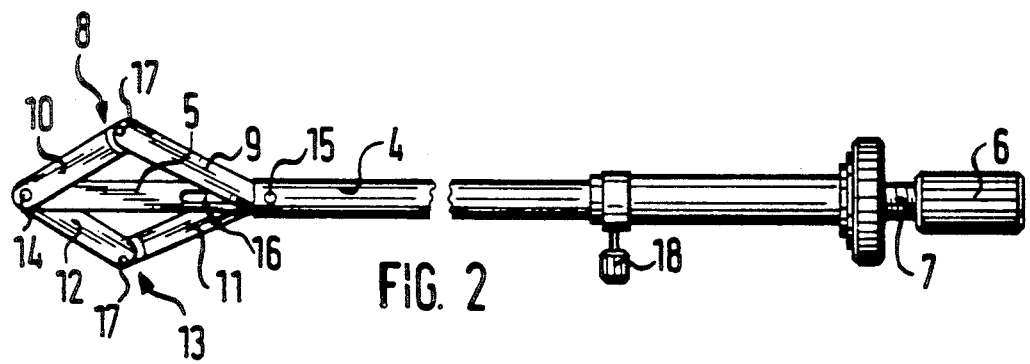
FIG. 2 shows a side view corresponding to FIG. 1 but with the retractor body in a partially retracted position.
Figure 3:
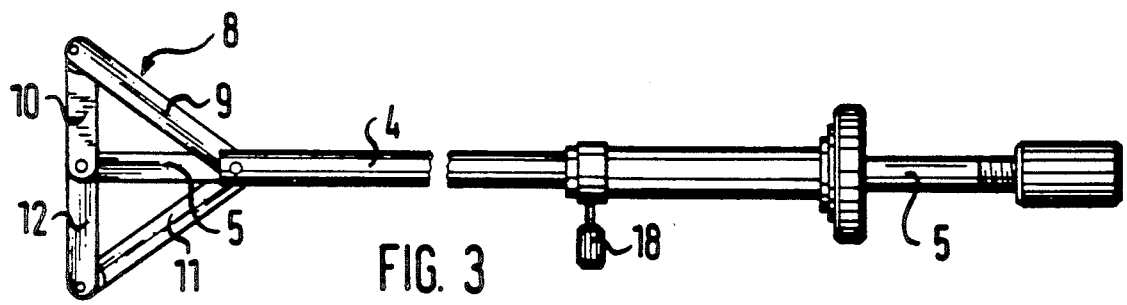
FIG. 3 shows a side view corresponding to FIG. 1 but with a fully retracted retractor body.

Referring to FIGS. 1 to 3, the manipulator 1 of the invention comprises a tubular handle part 2 with a radially rotatable and axially secured screw ring 3 at its proximal end. The handle part 2 is extended on the distal side by means of a tubular shaft 4. A rod 5, which also extends through the handle part 2 and is provided with a handle 6 at its proximal end and a thread 7 arranged in front of it, is displaceably mounted in the shaft 4. The rod 5 projects from the distal end of the shaft 4 and supports a retractor body 8 in the region of its distal end. This retractor body 8 comprises a multi-joint lever system of four articulated arms 9, 10, 11 and 12 connected to one another to be pivotally movable. In each case two of these articulated arms 9, 10 or 11, 12 are connected to one another by means of a central joint 13 and are assigned to opposing sides of the rod 5. In each case one end of the two articulated pairs 9, 10 or 11, 12 is thus pivotally connected to the distal end of the rod 5 and the other end is thus pivotally connected to the distal end of the shaft 4 by means of hinge pins 14 or 15, the latter engaging the rod 5 in the region of a longitudinal slot 16 arranged in it and being fixed to the shaft 4. The central joints 13 are formed by means or hinge pins 17 which are placed in the straight position of the articulated arms 9, 10 or 11, 12 on opposite sides of the plane of the central axis of the rod 5.

The retractor body is brought into the straight position to introduce the manipulator, for example through a trocar sleeve. This is achieved by the thread 7 in the region of the proximal end of the rod 5 being drawn into it by rotating the screw ring 3, and as a result the rod 5 is pushed out from the distal end of the shaft 4. Insertion may then be carried out, for example under observation through an endoscope introduced into the body cavity concerned elsewhere. When placed in the required position at or near the organ to be manipulated, the rod 5 may then be drawn into the shaft 4 by opposite rotation of the screw ring 3, with the effect that the distance of the hinge pins 14 and 15 from one another is reduced. The result is that the central joints 13 move out, this results in the hinge pins 17 in the straight position of the articulated arm pairs 9, 10 or 11, 12 not lying in the plane of the central axis of the rod 5, so that the draw-in movement of the same produces a component exposing the central joints 13. The retracting action directed radially outwards is additionally strengthened by one end of a spiral spring element (not shown) being fixed at each of the two ends of the articulated arms 9, 11, while the opposite other end is supported at the inner wall of the shaft 4 to rest loosely. The pulling movement transferred by means of the thread 7 may then be continued by disengaging the thread 7 and the screw ring 3 by removing the rod 5, until the hinge pin 15 comes to rest almost at the distal end of the longitudinal slot 16, which position produces approximately the maximum retracting position of the retractor body 8. By rotating the screw ring 3 in the opposite direction, a further thread (not shown) situated on the rod 5 at a distance from the thread 7 is drawn into it, this has the effect that the retractor body 8 is brought into its maximum retracting position and is fixed in this position.

A rinsing liquid may be introduced through the hose connection 18 situated at the distal end of the handle part 3 into the interior of the manipulator 1 to remove any impurities, and the manipulator is then sterilised. Furthermore, gas may be introduced into the body cavity through the hose connection 18.

To avoid image impairment caused by interfering reflections when a laser and a video transmission device are used at the same time and to achieve high absorption and scattering of the laser rays, the surface of the whole of the part of the instrument introduced into the body cavity is provided with a black coating which does not have a smooth surface.

Whilst a particular embodiment has been described, it should be appreciated that the invention is not limited thereto but includes all modifications and variations falling within its scope.

What is claimed is:

1. A medical instrument for manipulating internal organs of a body, comprising:
    a rod, having a retractor body arranged at a distal end of a rod and a handle at a proximal end of the rod;
    a rigid flexion resisting shaft, having a proximal end and a distal end, for guiding said rod, said rod being movable with respect to the shaft in an axial direction of said rod;
    wherein said retractor body comprises a multi-joint lever system of articulated arms connected to one another to be pivotably movable, which can be brought into an open position by movement of the rod in a first direction with respect to the shaft, and can be brought into a closed position by movement of the rod in a second direction with respect to the shaft.

2. A manipulator according to claim 1 wherein said multi-joint lever system comprises two pairs of articulated arms, each pair having a proximal end, a distal end and a central joint where two articulated arms are joined by a hinge, each pair being assigned to an opposite side of said rod guided by said shaft, said distal end of each pair being pivotally connected to said distal end of said rod and said proximal end of each pair being pivotally connected to said distal end of said shaft.

3. A manipulator according to claim 2, wherein said proximal end of each of said pair of articulated arms is pivotally connected to said distal end of said shaft by means of a hinge pin fixed in said distal end of said shaft and said rod has a slot arranged longitudinally on it, said hinge pin engaging said slot.

4. A manipulator according to claim 2, wherein said rod has a central axis and each of said pairs of articulated arms is joined, said distal ends of said pairs are joined to said distal end of said rod and said proximal ends of said pairs are joined to said distal end of said shaft by means of hinge pins wherein said hinge pins at said distal end of said rod and at said distal end of said shaft are arranged in said plane of a central axis of said rod and said hinge pins joining each of said pairs of articulated arms in the closed position of said articulated arms are arranged outside of said plane of said central axis of said rod.

5. A manipulator according to claim 2, wherein said articulated arms pivotally connected to said distal end of said rod each has an axis and act as exposing members for said pairs of articulated arms, said articulated arms pivotally connected to said distal end of said rod being essentially aligned along their axes with one another in a maximum retracting position.

* * * * *